(12) United States Patent
Hartley et al.

(10) Patent No.: US 8,021,419 B2
(45) Date of Patent: Sep. 20, 2011

(54) STENT GRAFT

(75) Inventors: David E. Hartley, Wannanup (AU); Timothy A. M. Chuter, San Francisco, CA (US)

(73) Assignee: Cook Medical Technologies LLC, Bloomington, IN (US)

( * ) Notice: Subject to any disclaimer, the term of this patent is extended or adjusted under 35 U.S.C. 154(b) by 29 days.

(21) Appl. No.: 12/377,438

(22) PCT Filed: Aug. 20, 2007

(86) PCT No.: PCT/US2007/018410
§ 371 (c)(1), (2), (4) Date: Mar. 12, 2009

(87) PCT Pub. No.: WO2008/021557
PCT Pub. Date: Feb. 21, 2008

(65) Prior Publication Data
US 2009/0319022 A1 Dec. 24, 2009

Related U.S. Application Data

(60) Provisional application No. 60/838,776, filed on Aug. 18, 2006.

(51) Int. Cl.
*A61F 2/06* (2006.01)
(52) U.S. Cl. ................... 623/1.35; 623/1.13
(58) Field of Classification Search .......... 623/1.27, 623/1.35, 1.15; *A61F 2/06*
See application file for complete search history.

(56) References Cited

U.S. PATENT DOCUMENTS

| | | | |
|---|---|---|---|
| 6,814,752 B1 | 11/2004 | Chuter | |
| 7,407,509 B2 * | 8/2008 | Greenberg et al. | 623/1.35 |
| 2003/0199967 A1 * | 10/2003 | Hartley et al. | 623/1.13 |
| 2004/0210296 A1 | 10/2004 | Schmitt | |
| 2004/0230287 A1 * | 11/2004 | Hartley et al. | 623/1.12 |
| 2006/0184228 A1 * | 8/2006 | Khoury | 623/1.13 |

FOREIGN PATENT DOCUMENTS

| | | |
|---|---|---|
| WO | WO03/082153 | 10/2003 |
| WO | WO2005/034808 | 4/2005 |

OTHER PUBLICATIONS

International Search Report and Written Opinion for PCT/US2007/018410.

\* cited by examiner

*Primary Examiner* — David Isabella
*Assistant Examiner* — Jason-Dennis Stewart
(74) *Attorney, Agent, or Firm* — Brinks Hofer Gilson & Lione

(57) ABSTRACT

A stent graft (10; 40; 80) has a tubular body (12; 42; 82) of a biocompatible material and at least two fenestrations (18, 20; 48, 50; 84, 86, 88). The at least two fenestrations (10, 20; 48, 50; 84, 86, 88) are adjacent each other and each has a tube {24, 26; 54, 55; 90, 92, 94) extending into the tubular body (1 2; 42; 82). The tubes (24, 26; 54, 55; 90, 92, 94) are joined inside the tubular body (12; 42; 82) into a single larger tube (30; 60; 96) to facilitate catheterization.

7 Claims, 5 Drawing Sheets

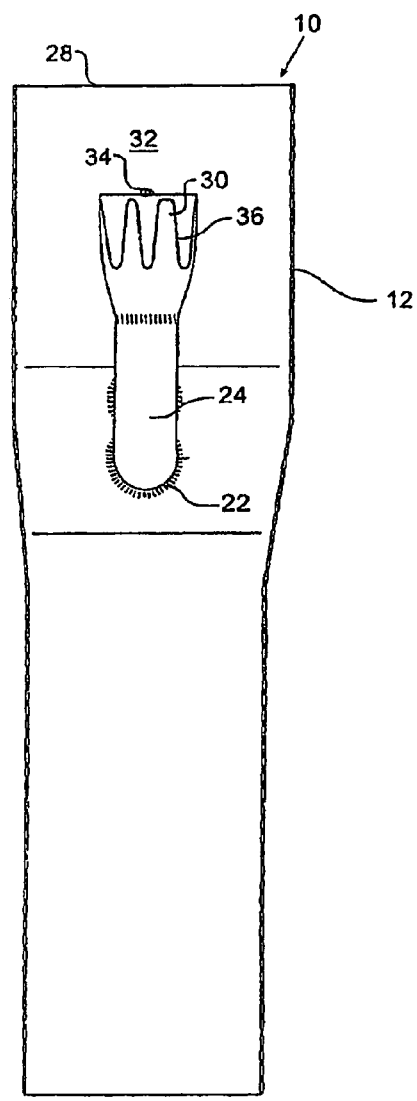
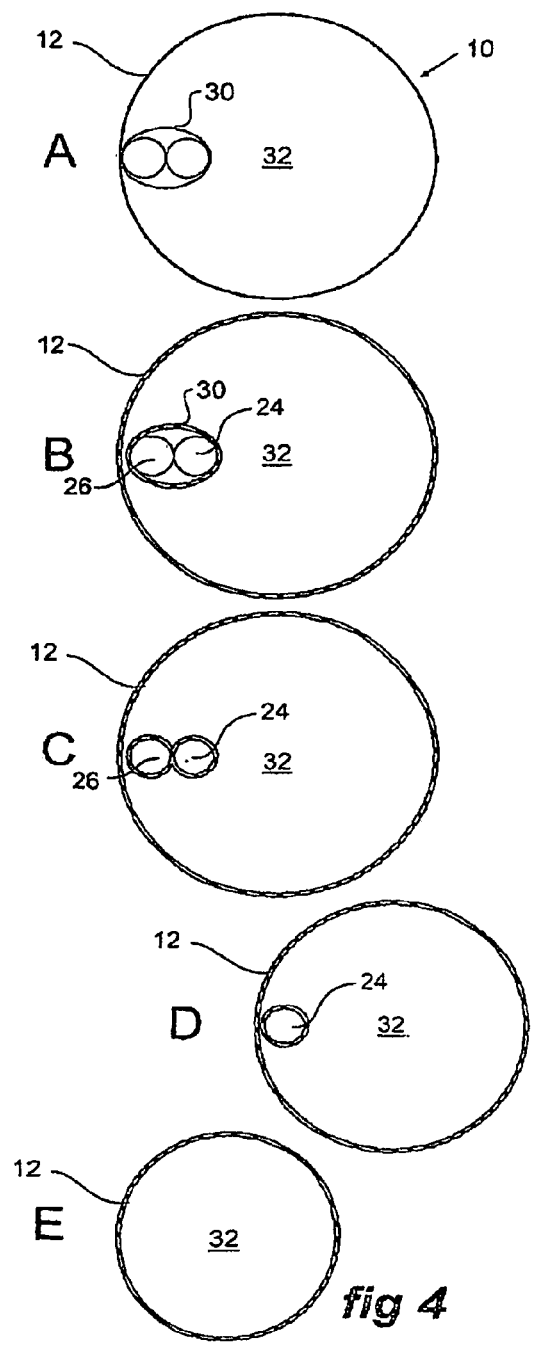
fig 3
fig 4

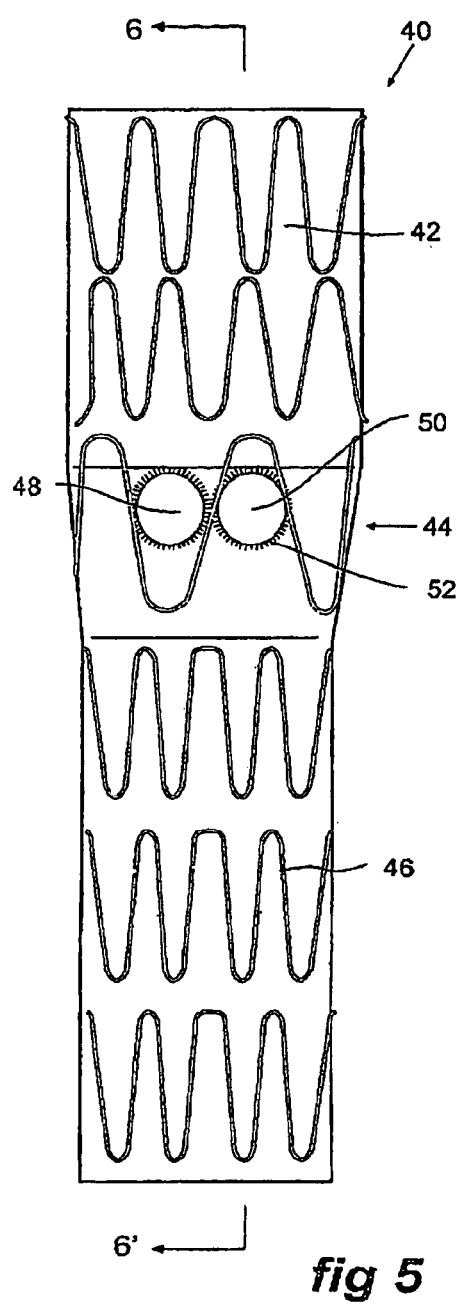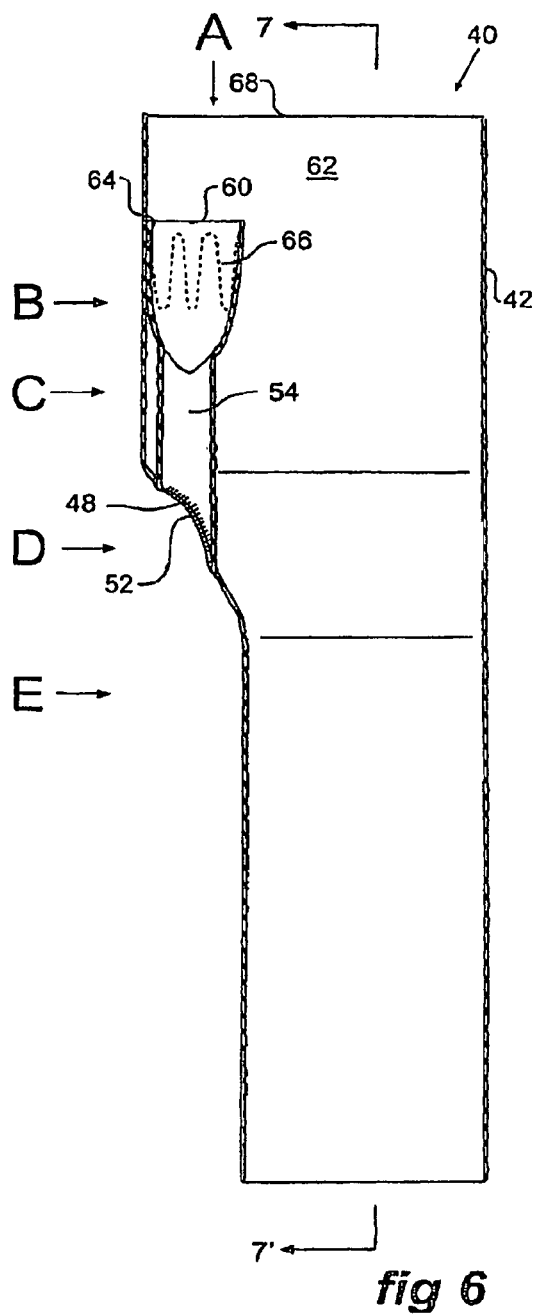
fig 5
fig 6

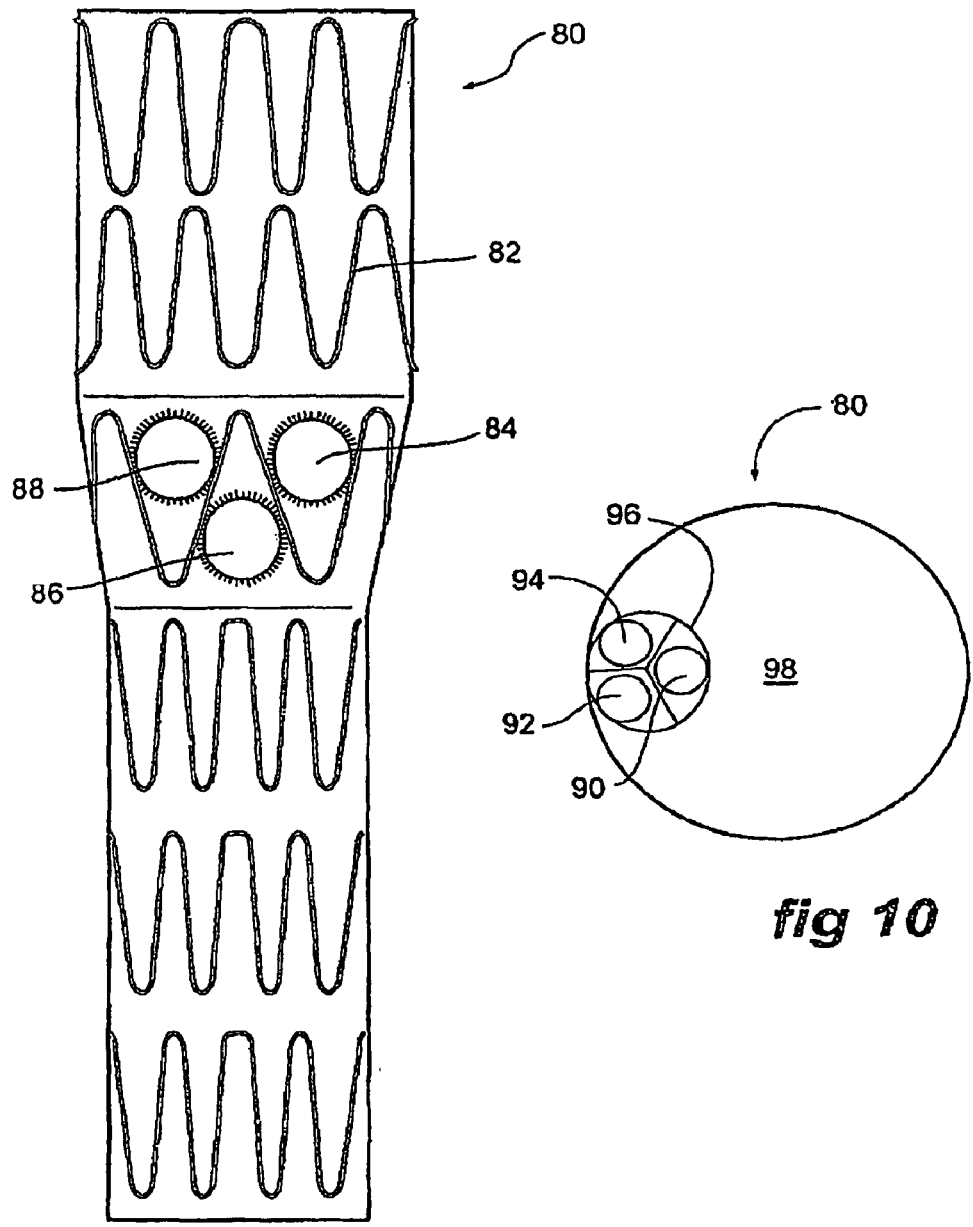

STENT GRAFT

RELATED APPLICATIONS

The present patent document is a §371 filing based on PCT Application Serial No. PCT/US2007/018410, filed Aug. 20, 2007 (and published as WO 2008/021557 A1 on Feb. 21, 2008), designating the United States and published in English, which claims the benefit of the filing date under 35 U.S.C. §119(e) of Provisional U.S. Patent Application Ser. No. 60/838,776, filed Aug. 18, 2006. All of the foregoing applications are hereby incorporated by reference in their entirety.

TECHNICAL FIELD

This invention relates to a medical device and more particularly to a stent graft for endovascular deployment. In particular, the invention relates to the configuration of branched stent grafts.

BACKGROUND OF THE INVENTION

Stent grafts have been devised for endovascular deployment to bypass a diseased portion of a vessel and such stent grafts can be deployed into body vessels such as the aorta. Where there are branches from the bodily vessel such as the aorta it is desirable to have a branch in the stent graft so that flow into the branch vessel is possible.

In the renal and suprarenal region of aorta, the use of a stent graft with branches extending from the stent graft is difficult and there have been proposed stent grafts with internal branches into which can be deployed a side arm extension to extend from the internal branch of the stent graft into a branch vessel.

It can be difficult however to catheterize such internal legs.

US 2004/210296 refers to a stent-graft, whereby a single tube of a larger diameter has side tubes that are branching off of the tube of larger diameter and fixed to the wall of the main tubular body of the stent-graft.

SUMMARY OF THE INVENTION

The present invention seeks to provide a stent graft with a construction that facilitates catheterization particularly where there are multiple branches to be connected. Preferred embodiments of the invention will be particularly discussed in relation to deployment of a stent graft into the renal and suprarenal regions of the aorta for deployment of a stent graft into the coeliac artery, the superior mesenteric artery and the renal arteries. However, the invention is not so limited and may be applied to other regions where there are branches from a main graft, such as in the thoracic arch.

Throughout this specification the term distal with respect to a portion of the aorta, a deployment device or a prosthesis is the end of the aorta, deployment device or prosthesis further away in the direction of blood flow from the heart, and the term proximal means the portion of the aorta, deployment device or end of the prosthesis nearer to the heart. When applied to other vessels similar terms such as caudal and cranial should be understood.

In one form, therefore, although this may not necessarily be the only or broadest form, an aspect of the invention provides a stent graft including a tubular body of a biocompatible material, at least two fenestrations in the tubular body, the at least two fenestrations being adjacent each other, a tube extending into the tubular body from each fenestration and the tubes being joined and opening into a single tube of larger diameter within the tubular body of the stent graft.

It will be seen that by having at least two tubes extending from fenestrations opening into a larger single tube, it is easier to catheterise by presenting a larger tube into which a guide wire can be deployed for instance by brachial access to enter the larger tube and subsequently one or other of the smaller tubes. The single tube of larger diameter thus acts as a guide to a catheter and provides a funnelling function to the at least two tubes.

In the case where the stent graft according to a preferred embodiment of the present invention is intended for use in the suprarenal region, the tubes extend toward the proximal end of the stent graft from the fenestration.

In a preferred embodiment the tubular body has a tapered portion and the fenestrations are provided in the tapered portion. In the region of the coeliac and superior mesenteric arteries, the aorta tapers as these major branch vessels extend from the aorta and tapering of the stent graft assists with maintaining a good blood flow and pressure in the stent graft.

The single tube of larger diameter is preferably joined to the wall of the tubular body so that it is held to one side of the lumen through the stent graft and can be relatively easily located using a guide wire.

In one embodiment, the at least two tubes may extend to positions that are adjacent laterally around the tubular body or that are adjacent longitudinally along the tubular body.

In an embodiment, there may be three fenestrations and three tubes extending to a single larger tube from the three fenestrations.

At least one of, and preferably each of, the fenestrations may include at least one reinforcing ring of nitinol wire therearound.

Preferably the single tube of larger diameter includes zig-zag self expanding stent and/or at least one of, and preferably each of, the tubes extending from the fenestrations also includes zig-zag self expanding stent. The zig-zag self-expanding stent may, in either case, be external.

BRIEF DESCRIPTION OF THE DRAWING

Preferred embodiments of the present invention are now described, by way of example only, with reference to the accompanying drawings, in which:

FIG. 3 shows a cross-sectional view of the stent graft of FIG. 1 along the lines 3-3' in FIG. 2;

FIGS. 4A to 4E show a top view and cross-sectional views at various levels as shown in FIG. 2;

FIG. 5 shows another embodiment of a stent graft;

FIG. 6 shows a cross-sectional view of the stent graft of FIG. 5 along the lines 6-6' of FIG. 5;

FIG. 9 shows another embodiment of a stent graft; and

FIG. 10 shows a view of the stent graft of FIG. 9 from the proximal end.

DETAILED DESCRIPTION

Figure 1:
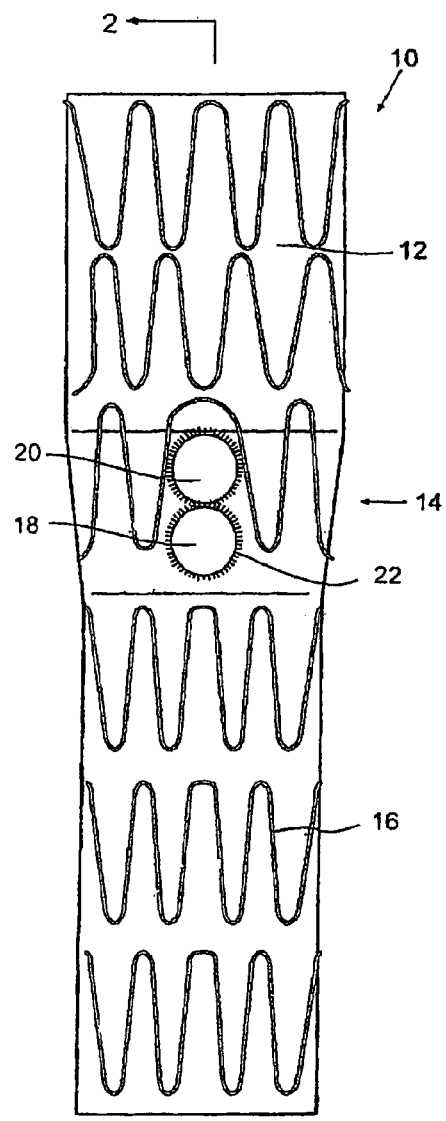
FIG. 1 shows a side view of a first embodiment of a stent graft.

Looking more closely at the drawings and in particular FIGS. 1 to 4 showing a first embodiment of a stent graft, it will be seen that stent graft 10 has a tubular body 12 of a biocompatible material, which includes a tapered central region 14. The tubular body is supported by stents 16. Preferably these stents are self expanding Gianturco zig-zag Z stents but other forms of stents may also be included or used.

In the tapered region 14, there are at least two fenestrations 18 and 20 defined by a resilient nitinol wire 22 around the periphery of the fenestration.

Figure 2:
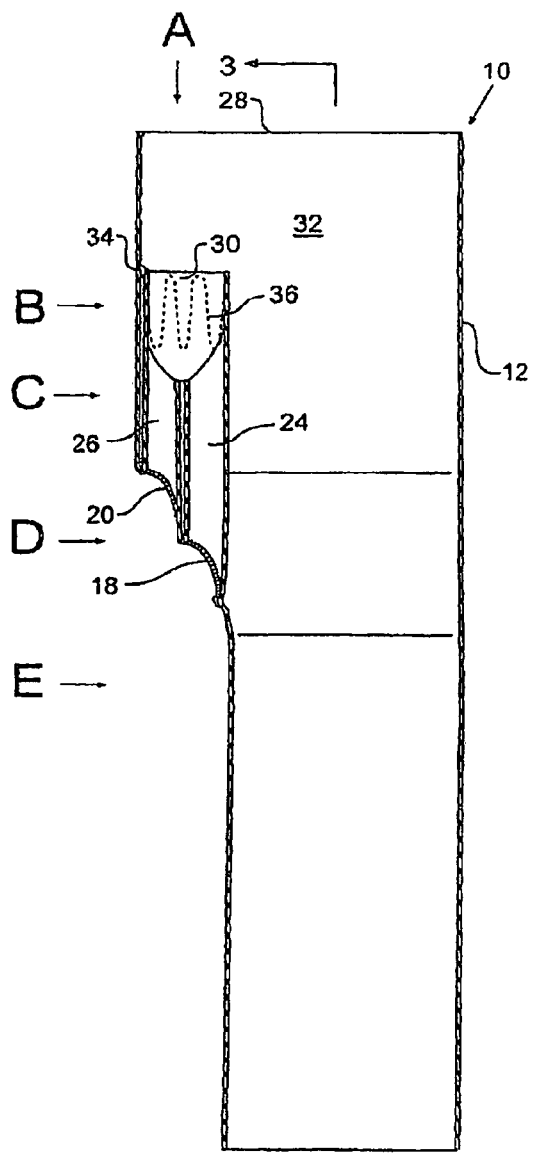
FIG. 2 shows a cross-sectional view of the stent graft of FIG. 1 along the lines 2-2' of FIG. 1.

As can be seen in FIG. 2, there are a pair of tubes 24 and 26 extending up from the fenestrations 18 and 20 towards the proximal end 28 of the stent graft 10 and these tubes 24 and 26 open into a single larger tube 30 which opens into the lumen 32 of the stent graft 10. The larger tube 30 is connected by stitching 34 to the tubular body 24 and a zig-zag self-expanding stent 36 is deployed around the outside of the larger body to enable or maintain patency once deployed and released within the human or animal body.

Although FIGS. 1 and 2 show a pair of tubes 24 and 26, there may be provided more than two of such tubes.

FIG. 4 shows various cross-sectional views of the stent graft shown in FIGS. 1 to 3.

A top view of the stent graft is shown in FIG. 4A. The stent graft tubular body 12 has the at least two tubes 24 and 26 opening into a single tube 30 and the single tube 30 is joined to the tubular wall 12 at 34 so that the tube 30 is held to one side of the tubular body.

FIG. 4B shows a cross-sectional view at the level B shown in FIG. 2. The larger tube 30 is shown in section and the smaller tubes 24 and 26 can be seen extending down from it within the lumen 32 of the stent graft tubular body 12.

FIG. 4C shows a cross-sectional view at the level C shown in FIG. 2. The smaller tubes 24 and 26 can be seen in cross-section within the lumen 32 of the stent graft tubular body 12.

FIG. 4D shows a cross-sectional view at the level D shown in FIG. 2. It can be seen that the tubular body 12 is of lesser diameter because the tubular body is in the tapered portion 14 and only the tube 24 can be seen in cross-section.

Further distally, at the cross-section E as shown in FIG. 4, the tubular body is substantially circular but of lesser diameter than further up.

The smaller tubes 24 and 26 could be provided with one or more self-expanding stents therein to maintain patency of the tubes once the stent graft has been deployed.

Now looking at FIGS. 5 to 8, showing an alternative embodiment of a stent graft according to the present invention, it will be seen that stent graft 40 has a tubular body 12 which includes a tapered central region 44. The tubular body is supported by stents 46. Preferably these stents are self-expanding Gianturco zig-zag Z stents but other forms of stents may also be included or used.

In the tapered region 14, there are at least two fenestrations 48 and 50 defined by a resilient nitinol wire 52 around the periphery of the fenestration.

Figure 7:
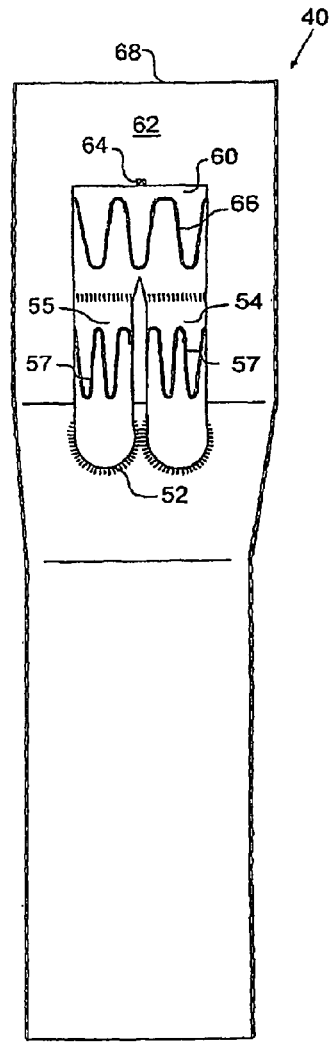
FIG. 7 shows a cross-sectional view of the stent graft of FIG. 5 along the lines 7-7' in FIG. 6.

As can be seen in FIGS. 6 and 7, there are a pair of tubes 54 and 55 extending up from the fenestrations 48 and 50 towards the proximal end 58 of the stent graft 40 and these tubes 54 and 55 open into a single larger tube 60 which opens into the lumen 62 of the stent graft 40. The larger tube 60 is connected by stitching 64 to the tubular body 44.

As with the first disclosed embodiment, this embodiment could also have more than two tubes 48, 50.

As can be particularly seen in FIG. 7 the larger tube 60 has a zig-zag self-expanding stent 66 deployed around the outside of the larger tube to enable or maintain patency once deployed and released within the human or animal body. The smaller tubes 54 and 55 extending from the fenestrations 48 and 50 also have zig-zag self expanding stents 57 deployed around their outsides to maintain patency of these tubes once the stent graft has been deployed and released within the human or animal body.

Figure 8:
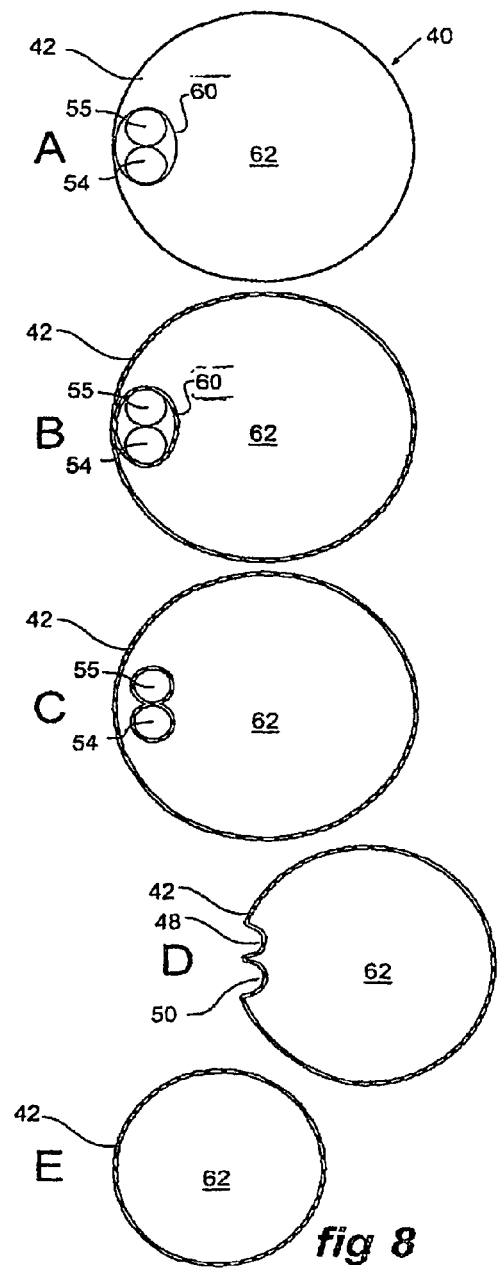
FIGS. 8A to 8E show a top view and cross-sectional views at various levels as shown in FIG. 6.

FIG. 8 shows various cross-sectional views of the stent graft shown in FIGS. 5 to 7.

A top view of the stent graft is shown in FIG. 8A. The stent graft tubular body 42 has the at least two tubes 54 and 55 opening into a single tube 60 and the single tube 60 is joined to the tubular wall 42 at 64 so that the tube 60 is held to one side of the tubular body.

FIG. 8B shows a cross-sectional view at the level B shown in FIG. 6. The larger tube 60 is shown in section and the smaller tubes 54 and 55 can be seen extending down from it within the lumen 62 of the stent graft tubular body 42.

FIG. 8C shows a cross-sectional view at the level C shown in FIG. 6. The smaller tubes 54 and 55 can be seen in cross-section within the lumen 62 of the stent graft tubular body 42.

FIG. 8D shows a cross-sectional view at the level D shown in FIG. 6. It can be seen that the tubular body 42 is of lesser diameter because the tubular body is in the tapered portion 44 and part of the tubes 54 and 55 can be seen in cross-section.

Further distally at the cross-section E as shown in FIG. 8 the tubular body is substantially circular but of lesser diameter than further proximally.

FIG. 9 shows another embodiment of the stent graft according to the present invention. In this embodiment the stent graft has a tubular body 80 supported by stents 82. In this embodiment there are at least three fenestrations 84, 86 and 88 and three tubes 90, 92, 94, extending from the fenestrations 84, 86 and 88 respectively. In this embodiment the fenestrations 84, 86 and 88 are arranged in a substantially triangular pattern.

As can be seen in FIG. 10, the three tubes 90, 92 and 94 open into a single larger tube 96 within the lumen 98 of the tubular body 80.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The invention claimed is:

1. A stent graft comprising:
   a tubular body of a biocompatible material;
   at least three fenestrations in the tubular body, the at least three fenestrations being adjacent each other and collectively forming a generally triangular shape; and
   a tube extending into the tubular body from each fenestration and the tubes being joined and opening into a single tube of larger diameter within the tubular body, wherein the tubes extend towards the proximal end of the stent graft from the fenestrations,
   wherein the single tube of larger diameter is joined to the wall of the tubular body so that it is held to one side of the lumen through the stent graft.

2. The stent graft of claim 1 wherein the tubular body has a tapered portion and the fenestrations are provided in the tapered portion.

3. A stent graft comprising:
   a tubular body of a biocompatible material;
   at least two fenestrations in the tubular body, the at least two fenestrations being adjacent each other;

a tube extending into the tubular body from each fenestration and the tubes being joined and opening into a single tube of larger diameter within the tubular body, wherein the tubes extend towards the proximal end of the stent graft from the fenestrations, wherein the single tube of larger diameter is joined to the wall of the tubular body so that it is held to one side of the lumen through the stent graft, wherein the single tube of larger diameter includes an external zig-zag self-expanding stent, wherein each of the at least two tubes include at least one external zig-zag self-expanding stent thereon, and wherein the stents of the at least two tubes are longitudinally spaced apart from the stent of the single tube of larger diameter.

4. The stent graft of claim 3 wherein the tubular body has a tapered portion and the fenestrations are provided in the tapered portion.

5. The stent graft of claim 3 wherein the at least two tubes extend to positions that are adjacent one another laterally around the tubular body.

6. The stent graft of claim 3 wherein the at least two tubes extend to positions that are adjacent one another longitudinally along the tubular body.

7. The stent graft of claim 3 comprising at least three fenestrations in the tubular body and at least three tubes extending from the fenestrations to the single tube of larger diameter.

* * * * *